United States Patent
Yasuno et al.

(10) Patent No.: US 6,319,680 B1
(45) Date of Patent: Nov. 20, 2001

(54) METHOD FOR ANALYZING MONOSACCHARIDE IN A SUGAR COMPOSITION

(75) Inventors: Shoichi Yasuno, Yokohama; Masugu Kamei, Fujisawa; Junko Arai, Zushi; Keiko Saito, Yokohama, all of (JP)

(73) Assignees: Kabushiki Kaisha Honen Corporation, Tokyo; Zaidanhojin Sugiyama Sangyo Kagaku, Yokohama, both of (JP)

( * ) Notice: Subject to any disclaimer, the term of this patent is extended or adjusted under 35 U.S.C. 154(b) by 0 days.

(21) Appl. No.: 09/556,682

(22) Filed: Apr. 21, 2000

(30) Foreign Application Priority Data

May 28, 1999 (JP) ................................. 11-149720

(51) Int. Cl.$^7$ ............................... C12Q 1/34; C12Q 1/00
(52) U.S. Cl. ................... 435/18; 435/4; 435/195; 435/200; 435/232
(58) Field of Search ................. 435/18, 4, 195, 435/200, 232

(56) References Cited

PUBLICATIONS

Fu et al, Analytical Biochemistry 227:377–384, 1995.*

Tomohiro Mega and Tokuji Ikenaka, *Methanolysis Products of Asparagine–Linked N–Acetylglucosamine and a New Method for Determination of N– and O–Glycosidic N–Acetyglucosamine in Glycoproteins That contain Asparagine–Linked Carbohydrates*, Department of Chemistry, Osaka University College of Science, Toyonaka, Osaka 560, Japan Received Jun. 9, 1981, Analytical Biochemistry 119, 17–24 (1982).

*Method for Studying Glycoprotein Sugar Chain* (Biochemistry Experimental Methods 23), Gakkai Shuppan Center, p. 20 (1989).

Mark R. Hardy and R. Reid Townsend *Guide to Techniques in Glycobiology*, "[12]High–pH Anion–Exchange Chromatography of Glycoprotein–Derived Carbohydrates" Methods in Enzymology, vol. 230, 208–225 (1994).

Chemistry of Proteins, first volume (Continued Biochemical Experiment Thesis 2, ed, by Japan Biochemical Society Tokyo Kagaku Dojin, p. 215–218)(1987).

Sidney P. Colowick and Nathan O. Kaplan *"Methods in Enzymology"*, vol. 25, pp. 244 (1972).

Shuuji Hara, *Yasuyo Takemori, *Masatoshi Yamaguchi, *2 Masaru Nakamura, *and Yosuke Ohkura *Fluorometric High–Performance Liquid Chromatography of N–Acetyl–l–and N–Glycolylneuraminc Acids and its Application to Their Microdetermination in Human and Animal Sera, Glycoproteins, and Glycolipids1*.

Continued Biochemical Experiment Thesis (2), *Chemistry of Protein*, vol. 2, edited by Nihon Seikagakukai, published by Tokyo Kagaku Dojin, 1987, pp. 215–218. (English Translation).

Biochemical Experimental Method 23, *Method for Studying Glycoprotein Sugar Chain*, edited by Kunizo.

Tsumetani, et al., published by Gakkai Shuppan Center, 1989, p. 20. (English Translation).

\* cited by examiner

*Primary Examiner*—Francisco Prats
(74) *Attorney, Agent, or Firm*—Oliff & Berridge, PLC

(57) ABSTRACT

A method for the determination of monosaccharides in a sugar composition by simultaneous quantitative analysis of monosaccharides constituting the sugar composition, comprising the steps of: (1) liberating sialic acid from the sugar composition with sialidase or an acid, (2) converting the released sialic acid into N-acylmannosamine with sialic acid aldolase, and (3) acid hydrolyzing the N-acylmannosamine and a sugar residue. The method allows pretreatment in a single reactor and the sugar composition including sialic acid can be obtained by a single analysis by HPLC, etc.

24 Claims, No Drawings

METHOD FOR ANALYZING MONOSACCHARIDE IN A SUGAR COMPOSITION

BACKGROUND OF THE INVENTION

1. Field of the Invention

The present invention relates to a method for the quantitative determination of a monosaccharide, such as sialic acid, constituting a sugar composition.

2. Description of Related Art

Sugar compositions such as glycoproteins and glycolipids are important substances that constitute a mechanism of function-regulation for human body, particularly immunity related portions and, recently, investigations have been being made intensively in the top front of medicine, such as therapy of AIDS or tumors. It has already been considered that the sugar chain of glycoprotein present on the surface of AIDS virus bonds to the CD4 molecule on the surface of host cells to cause infection and there have been many reports that the sugar moiety of the sugar composition varies due to tumors.

Among such methods, particularly quantitative determination of various monosaccharides constituting the sugar composition composed mainly of sialic acid is the key of the investigation and various methods have been proposed for achieving more rapid and higher sensitivity analysis.

Various conventional methods and their advantages and disadvantages will be explained below.

For example, (1) A method for determining sialic acid, neutral sugars and amino sugars by gas-liquid chromatography (GLC) after converting the sample into a volatile sugar derivative by methanolysis and trimethylsilylation:

This method has defects that although it can determine sialic acid, neutral sugars and amino sugars simultaneously, it requires a large amount of sample (10 nmol or more as monosaccharide), that the analysis by GLC is not suitable for treating multiple samples, and that N-acetylglucosamine bonded to an asparagine residue cannot be determined (Anal. Biochem., 119, 17–24 (1982)).

(2) A method for the determination of sialic acid in which sialic acid liberated by sialidase or an acid is converted to 1,2-diamino-4,5-methylenedioxybenzene acid (DMB) derivative, followed by high performance liquid chromatography (HPLC):

This method is simple and has high sensitivity. However, it can analyze only sialic acid and the derivative is unstable and has to be analyzed within 12 hours ("Method for Studying Glycoprotein Sugar Chain (Biochemistry Experimental Methods 23)", Gakkai Shuppan Center, p.20 (1989)) and is limited in its application.

(3) A method for the determination of amino sugars by amino acid analysis:

This method is simple and has high sensitivity but it can analyze only amino sugars.

(4) A method for the determination of neutral sugars and amino sugars that involves labeling the sugars with pyridylamino, converting them into ethyl 4-aminobenzoate derivatives, followed by HPLC:

This method cannot analyze sialic acid.

(5) A method for the determination of sialic acid, neutral sugars and amino sugars by converting the sialic acid and sugars into 1-phenyl-3-methyl-5-pyrazolone (PMP) derivative, followed by HPLC:

This method can be determined with high sensitivity, but has such an inconvenience that sialic acid can not be simultaneously determined together with neutral sugars and amino sugars.

(6) A method for the determination of sialic acid, neutral sugars and amino sugars that involves converting the sialic acid and sugars into cyanoacetamide derivatives after isolation by HPLC:

This method is a post column labeling method and is simple but takes a long time for analysis and cannot afford simultaneous determination of sialic acid together with neutral sugars and amino sugars so that it is inconvenient.

(7) A method for the determination of sialic acid, neutral sugars and amino sugars using anion exchange chromatography and an electrochemical detector:

This method can save the trouble of labeling but it is inconvenient in that it requires a special apparatus and that it cannot determine sialic acid together with neutral sugars and amino sugars simultaneously (Methods in Enzymology, 230, 208–225 (1994)).

As stated above, conventional methods for the determination of monosaccharides constituting sugar compositions are advantageous in a way and disadvantageous in another. Whereas the method for the determination of sugar compositions that enables diagnosis of affected sites without surgical invasion gives less stress to patients and hence are being increasingly used. Thus, a method that can treat many samples in a simple manner is desired. Accordingly, there has been a keen desire for urgently developing a method for simultaneous determination of monosaccharides that constitute sugar compositions including sialic acid that has recently attracted much attention as an indices for monitoring changes in pathological state affected by, e.g., tumors, with high rate, high sensitivity and accuracy.

BRIEF SUMMARY OF THE INVENTION

Therefore, it is an object of the present invention to provide a method for the simultaneous determination of monosaccharides constituting a sugar composition.

With view to solving the above object, the present inventors have made intensive research and as a result they have found that in the analysis of monosaccharides in a sugar composition such as glycoprotein, glycolipid, etc. which are constituted by bonding of respective monosaccharides, etc., a sialic acid and respective monosaccharides can be determined simultaneously by converting liberated sialic acid into N-acylmannosamine followed by acid hydrolysis, thus achieving the present invention.

That is, the present invention provides a method for analyzing monosaccharides in a sugar composition, comprising the steps of:

(1) liberating sialic acid from the sugar composition with sialidase or an acid;

(2) converting the liberated sialic acid into N-acylmannosamine with sialic acid aldolase; and (3) acid hydrolyzing N-acylmannosamine and a sugar residue.

Furthermore, in the present invention, upon determination of the respective monosaccharides, the de-N-acylated monosaccharides during hydrolyss may be N-acetylated, and further the monosaccharides that are N-acetylated again and N-acylmannosamine may be labeled with ethyl 4-aminobenzoate (ABEE).

In the above description, the sugar residue means a remaining sugar composition after only sialic acid is liberated from a sugar composition to be determined, i.e., a bonded substance of remaining monosaccharides.

The sialic acid (N-acylmannosamine) and the respective monosaccharides may be analyzed by MPLC, capillai electrophoresis, GLC or the like method. It is particularly preferred that they are analyzed by HPLC, which is suitable for treating many samples.

In the present invention, the determination of respective monosaccharides by HPLC may be performed using a reverse phase column and it is desirable to use a borate buffer as an eluent.

DETAILED DESCRIPTION OF THE INVENTION

According to the present invention, sialic acid and respective monosaccharides constituting a sugar composition can be determined simultaneously. In the conventional methods, sialic acid was completely decomposed and could not be detected under the conditions under which neutral sugars and amino sugars are hydrolyzed. Therefore, when sialic acid, neutral sugars and amino sugars are determined, treatment and analysis must have been performed twice or more on a single sample. In the present invention, sialic acid is preliminarily converted into a compound which is not decomposed under the condition that neutral sugars and amino sugars are hydrolyzed, so that the determination of sialic acid, neutral sugars and amino sugars at a time. This provides excellent operability and enables rapid determination of respective monosaccharides constituting a sugar composition.

The sugar composition, which is the target of analysis in the present invention, includes glycoproteins, glycolipids, oligosaccharides and polysaccharides.

The reagent used in the present invention includes sialidase, sialic acid aldolase and acids. Sialidase may be originated from *Arthrobacter ureafaciens, Clostridium perfringens, Streptococcus s., Vibrio cholerae, Salmonella typhimurium*, New castle disease virus, etc. The reagent originated from *Arthrobacter ureafaciens*, which is easy to handle, is desirable. The sialic acid aldolase may be originated from *Escherichia coli, Clostiridium perfringens*, etc. Desirably, it is originated from *Escherichia coli*, which is easy to handle. The acid which can be used includes trifluoroacetic acid, hydrochloric acid, sulfuric acid, etc. Desirably, the acid is trifluoroacetic acid, which can be easily removed is preferable.

In practicing the present invention, liberation of sialic acid from a sugar composition and conversion of the liberated sialic acid into N-acylmannosamine can be carried out by successive addition of sialidase or acid and sialic acid aldolase into a reactor containing the sugar composition or by simultaneous addition of these reagents. Thereafter, sugar residue in which sialic acid is liberated and N-acylmannosamine are hydrolyzed by adding an acid, and the obtained hydrolyzed products are analyzed by HPLC, etc., whereby determining respective monosaccharides which constitute a sugar composition.

Upon quantitative analysis of monosaccharides, the de-N-acylated monosaccharide by the above hydrolysis may be preliminarily N-acetylatec or the sialic acid and the respective monosaccharides liberated may be labeled with ABPE before quantitative analysis can be done.

In the present invention, the respective treatments of samples can be carried out without changing the reactor but may be performed in the same reactor.

Hereinafter, the present invention will be explained in more detail by illustrative examples and the gist of the present invention should not be construed as being limited thereto.

EXAMPLE 1

Ten (10) $\mu$l (5 $\mu$g) of fetuin (manufactured by Sigma Chemical Co., U.S.A.) originated from calf serum was charged in a screw-openable test tube (45 mm×9.5 mm I.D.) and evaporated to dryness under reduced pressure. In the test tube were added 5 $\mu$l of a sialic acid aldolase solution and 5 $\mu$l of a sialidase solution and the mixture was kept at 37° C. for 17 hours. Further, 10 $\mu$l of aqueous 8M trifluoroacetic acid solution was added to a final concentration of 4 M, and the mixture was kept at 121° C. for 2 hours. After air-cooling, the mixture was evaporated to dryness under reduced pressure and then 100 $\mu$l of 2-propanol was added in order to remove the acid sufficiently. Again, the mixture was evaporated to dryness under reduced pressure. To the resulting product was added 40 $\mu$l of pyridine/methanol (5/95, volume ratio (v/v)) and then 10 $\mu$l of acetic anhydride. The mixture was left to stand at room temperature for 30 minutes to perform N-acetylation, followed by evaporation to dryness under reduced pressure.

After addition of 10 $\mu$l of deionized water and 40 $\mu$l of ABEE labeling reagent (manufactured by Seikagaku Kogyo Kabushiki Kaisha, Japan), the mixture was kept at 80° C. for 1 hour. After addition of 200 $\mu$l of deionize water and 200 $\mu$l of chloroform, the mixture was centrifuged. The supernatant was subjected to HPLC analysis. <HPLC Analysis Conditions>

The HPLC feed pump, controller, column oven and fluorescence detector used were manufactured by Shimadzu Corporation, Japan). As the column, Honenpak C18 (manufactured by Seikagaku Kogyo Kabushiki Kaisha, Japan) which is a reverse phase column, was used and chromatography was performed at a flow rate of 1 ml/min at a column temperature of 30° C. For the mobile phase was used 0.2 M potassium borate buffer (pH 8.9)/acetonitrile (93/7, v/v). Detection was performed at an excitation wave-length of 305 nm and at an emission wave-length of 360 nm.

EXAMPLE 2

Ten (10) $\mu$l (5 $\mu$g) of a calf serum-derived fetuin (manufactured by Sigma Chemical Co., U.S.A.) solution was charged in a screw-openable test tube (45 mm×9.5 mm I.D.). To this was added 10 $\mu$l of aqueous 0.2 M trifluoroacetic acid solution and the mixture was stirred and kept at 80° C. for 1 hour to liberate sialic acid.

After removing the trifluoroacetic acid under reduced pressure, 10 $\mu$l of sialic acid aldolase solution was added and the mixture was kept at 37° C. for 17 hours. Further, 10 4$\mu$l of an aqueous 8M trifluoroacetic acid solution was added to a final concentration of 4 M and the mixture was kept at 121° C. for 2 hours. After air-cooling, the mixture was evaporated to dryness under reduced pressure. Thereafter, to remove the trifluoroacetic acid sufficiently, 100 $\mu$l of 2-propanol was added and again the mixture was evaporated to dryness under reduced pressure. To the resulting product was added 40 $\mu$l of pyridine/methanol (5/95, v/v) and then 10 $\mu$l of acetic anhydride. The resulting mixture was left to stand at room temperature for 30 minutes to perform N-acetylation, followed by evaporation to dryness under reduced pressure.

After addition of 10 $\mu$l of deionized water and 40 $\mu$l of ABEE labeling reagent (manufactured by Seikagaku Kogyo Kabushiki Kaisha, Japan), the mixture was kept at 80° C. for 1 hour. After addition of 200 $\mu$l of deionized water and 200 $\mu$l of chloroform, the mixture was centrifuged and the supernatant was subjected to HPLC analysis. The HPLC analysis was conducted under the same conditions as in Example 1.

EXAMPLE 3

The same procedures as in Example 2 were repeated for the analysis of monosaccharides except that the calf serum-derived fetuin (manufactured by Sigma Chemical Co., U.S.A.) was replaced by II$^3$NeuGc α-LacCer (Wako Junyaku Kogyo Kabushiki Kaisha, Japan), a glycolipid, was used.

EXAMPLE 4

The same procedures as in Example 2 was similarly conducted for the analysis of monosaccharides except that 3'-sialyllactose (manufactured by Sigma Chemical Co., U.S.A.) was used in place of the fetuin derived from calf serum (manufactured by Sigma Chemical Co., U.S.A.).

COMPARATIVE EXAMPLE 1

Sixty (60) μg of calf serum-derived fetuin (manufactured by Sigma Chemical Co., U.S.A.) was kept in 100 μl of 1.4 M hydrochloric acid methanol solution at 90° C. for 2 hours. Hydrochloric acid and methanol were removed under a stream of nitrogen. To the resulting product were added 200 μl of 10% pyridine-methanol and 10 μl of acetic anhydride and the mixture was left to stand at room temperature for 30 minutes. Under reduced pressure, the solvent was removed and 50 μl of trimethylsilylating reagent (Tri-Sil manufactured by Pierce Chemical Co., U.S.A.) was added. The resulting mixture was kept at 46° C. for 10 minutes. In the presence of sulfuric acid, the solvent was removed under reduced pressure, the residue was extracted with n-pentane, and the extract was concentrated. Thereafter, the concentrate was subjected to gas chromatography analysis using a 2% OV-17 (Uniport HP (60/80)) column (manufactured by GL Sciences Inc., Japan) ("Chemistry of Proteins, first volume (Continued Biochemical Experiment Thesis 2)", ed. by Japan Biochemical Society, Tokyo Kagaku Dojin, p. 215–218) (1987).

COMPARATIVE EXAMPLE 2

Ten (10) μg of calf serum-derived fetuin (manufactured by Sigma Chemical Co., U.S.A.) was kept in 40 μl of 6N hydrochloric acid at 100° C. for 6 hours. Then, the acid was removed under reduced pressure. The treated product was labeled with 6-aminoquinolyl-N-hydroxysuccinimidyl carbamate using AccQ labeling reagent (manufactured by Waters Corp., U.S.A.) and the labeled product was analyzed by HPLC according to the annexed manual.

COMPARATIVE EXAMPLE 3

Five (5) μg of calf serum-derived fetuin (manufactured by Sigma Chemical Co., U.S.A.) was incubated in 20 μl of an aqueous 0.1 M trifluoroacetic acid solution at 80° C. for 1 hour. Then, the treated product was labeled with 1,2-diamino-4,5-methylenedioxybenzene (DMB) using DMB labeling reagent (manufactured by Takara Shuzo Kabushiki Kaisha, Japan) and the labeled product was analyzed by HPLC according to the annexed manual.

The results of analyses obtained in each of Examples and Comparative Examples above are shown in Tables 1 and 2.

TABLE 1

Monosaccharide composition of fetuin derived from calf serum (mol/mol)[*1]

| Method | galactose | mannose | fucose | GlcNAc | GalNAc | sialic acid |
|---|---|---|---|---|---|---|
| Example 1 | 9.5 | 7.7 | n.d.[*2] | 11.2 | 2.0 | 10.5 |
| Example 2 | 9.5 | 8.0 | n.d. | 10.9 | 2.0 | 10.3 |
| Comparative Example 1 | 9.6 | 7.8 | n.d. | 8.1 | 2.5 | 12.2 |
| Comparative Example 2 | —[*3] | — | — | 10.8 | 1.9 | — |
| Comparative Example 3 | — | — | — | — | — | 10.4 |

Note)
[*1] mol/mol; calculated on the basis of a molecular weight of 48,400.
[*2] n.d. means "not detectable"
[*3] — means monosaccharide which was not determined.
GlcNAc: N-acetylglucosamine
GalNAc: N-acetylgalactosamine

TABLE 2

Monosaccharide compositions of II$^3$NeuGc α-LacCer and 3'-sialyllactose

|  | galactose | glucose | sialic acid |
|---|---|---|---|
|  |  | (molar ratio)[*1] |  |
| II$^3$NeuGc α-LacCer |  |  |  |
| Example 3 | 1.0 | 1.0 | 0.9 |
| known molar ratio | 1.0 | 1.0 | 1.0 |
| 3'-sialyllactose |  |  |  |
| Example 4 | 1.0 | 0.9 | 1.0 |
| known molar ratio | 1.0 | 1.0 | 1.0 |

[*1] molar ratio: molar ratios were indicated in conditions that molar ratio of galactose was 1.0.

As shown in Table 1, when the method of the present invention was used (Examples 1 and 2), a composition of sialic acid, neutral sugars and amino sugars in the sugar composition could be obtained by a single analysis. On the other hand, in Comparative Example 1, no accurate results could be obtained on N-acetylglucosamine (GlcNAc). Furthermore in Comparative Example 2, only amino sugars could be determined, and in Comparative Example 3, determination values on sialic acid only could be obtained. In other words, no accurate composition of sialic acicd, neutral sugars and amino sugars in the sugar composition could be obtained by use of the conventional methods unless at least two kinds of methods are used.

Furthermore, as shown in Table 2, the results obtained by use of the method of the present invention (Examples 3 and 4) not only show that the methods of the present invention can be applied to glycolipids and oligosaccharides but also indicate that they are methods that can give very accurate results.

What is claimed is:

1. A method of identifying monosaccharides present in a sugar-containing compound, and quantitatively analyzing the amounts of the respective monosaccharides present, comprising:
   contacting a sugar-containing compound with sialidase or acid thereby producing a first mixture comprising sialic acid and a sialidase-treated sugar-containing compound or acid-treated sugar-containing compound;

converting the produced sialic acid into N-acylmannosamine by contacting the produced sialic acid with sialic acid aldolase, thereby producing a second mixture comprising N-acylmannosamine and a sialidase-treated or acid-treated sugar-containing compound;

acid hydrolyzing the second mixture; and analyzing the resulting acid hydrolyzate to determine the identities and amounts of monosaccharides present in the acid hydrolyzate.

2. The method of claims 1, wherein the sugar-containing compound is a glycoprotein.

3. The method of claim 1, wherein the sugar-containing, compound is a glycopeptide.

4. The method of claim 1, wherein the sugar-containing compound is a glycolipid.

5. The method of claim 1, wherein the sugar-containing compound is a oligosaccharide.

6. The method of claim 1, wherein the sugar-containing compound is a polysaccharide.

7. The method of claim 1, wherein analyzing the resulting acid hydrolyzate comprises conducting high performance liquid chromatography (HPLC).

8. The method of claim 7, wherein conducting HPLC comprises using a reverse phase column and a borate buffer as an eluent.

9. A method of identifying monosaccharides present in a sugar-containing compound, and quantitatively analyzing the amounts of the respective monosaccharides present, comprising:

contacting a sugar-containing compound with sialidase or acid, thereby producing a first mixture comprising sialic acid and a sialidase-treated sugar-containing compound or acid-treated sugar-containing compound;

converting the produced sialic acid into N-acylmannosamine by contacting the produced sialic acid with sialic acid aldolase, thereby producing a second mixture comprising N-acylmannosamine and a sialidase-treated or acid-treated sugar-containing compound;

acid hydrolyzing the second mixture;

N-acetylating de-N-acylated monosaccharides present in the resulting acid hydrolyzate, thereby producing a third mixture; and analyzing the third mixture to determine the identities and amounts of monosaccharides present the third mixture.

10. The method of claim 9, wherein the sugar-containing compound is a glycoprotein.

11. The method of claim 9, wherein the sugar-containing compound is a glycopeptide.

12. The method of claim 9, wherein the sugar-containing compound is a glycolipid.

13. The method of claim 9, wherein the sugar-containing compound is a oligosaccharide.

14. The method of claim 9, wherein the sugar-containing compound is a polysaccharide.

15. The method of claim 9, wherein analyzing the third mixture comprises conducting high performance liquid chromatography (HPLC).

16. The method of claim 15, wherein conducting HPLC comprises using a reverse phase column and a borate buffer as an eluent.

17. A method of identifying monosaccharides present in a sugar-containing compound and quantitatively analyzing the amounts of the respective monosaccharides present comprising:

contacting a sugar-containing compound with sialidase or acid, thereby producing a first mixture comprising sialic acid and a sialidase-treated sugar-containing compound or acid-treated sugar-containing compound;

converting the produced sialic acid into N-acylmannosamine by contacting the produced sialic acid with sialic acid aldolase, thereby producing a second mixture comprising N-acylmannosamine and a sialidase-treated or acid-treated sugar-containing compound;

acid hydrolyzing the second mixture;

N-acetylatiing de-N-acylated monosaccharides present in the resulting acid hydrolyzate, thereby producing a third mixture;

labeling monosaccharides present in the third mixture with ethyl 4-aminobenzoate (ABEE), thereby creating a fourth mixture; and analyzing the fourth mixture to determine the identities and amounts of monosacchrides present in the acid hydrolyzate.

18. The method of claim 17, wherein the sugar-containing compound is a glycoprotein.

19. The method of claim 17, wherein the sugar-containing compound is a glycopeptide.

20. The method of claim 17, wherein the sugar-containing compound is a glycolipid.

21. The method of claim 17, wherein the sugar-containing compound is a oligosaccharide.

22. The method of claim 17, wherein the sugar-containing compound is a polysaccharide.

23. The method of claim 17, wherein analyzing the fourth mixture comprises conducting high performance liquid chromatography (HPLC).

24. The method of claim 23, wherein conducting HPLC comprises using a reverse phase column and a borate buffer as an eluent.

\* \* \* \* \*